(12) United States Patent
Zhou et al.

(10) Patent No.: US 12,104,189 B2
(45) Date of Patent: Oct. 1, 2024

(54) **MUTANT OF NITRILE HYDRATASE DERIVED FROM *CALDALKALIBACILLUS THERMARUM***

(71) Applicant: Jiangnan University, Wuxi (CN)

(72) Inventors: Zhemin Zhou, Wuxi (CN); Zhongmei Liu, Wuxi (CN); Ting Li, Wuxi (CN); Dezhi Chen, Wuxi (CN); Sailan Zhang, Wuxi (CN); Li Zhou, Wuxi (CN); Wenjing Cui, Wuxi (CN); Zhongyi Cheng, Wuxi (CN); Junling Guo, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 479 days.

(21) Appl. No.: 17/399,423

(22) Filed: Aug. 11, 2021

(65) Prior Publication Data

US 2021/0388336 A1 Dec. 16, 2021

Related U.S. Application Data

(63) Continuation of application No. PCT/CN2019/114605, filed on Oct. 31, 2019.

(51) Int. Cl.
*C12N 9/88* (2006.01)
*C12N 1/20* (2006.01)

(52) U.S. Cl.
CPC .............. *C12N 9/88* (2013.01); *C12N 1/20* (2013.01); *C12Y 402/01084* (2013.01)

(58) Field of Classification Search
CPC ..................................... C12N 1/20; C12N 9/88
See application file for complete search history.

(56) References Cited

U.S. PATENT DOCUMENTS

2011/0104690 A1 5/2011 Yu et al.

FOREIGN PATENT DOCUMENTS

| CN | 104830747 A | * | 8/2015 | |
|---|---|---|---|---|
| CN | 107177581 A | | 9/2017 | |
| CN | 109251882 A | | 1/2019 | |
| CN | 109593750 A | | 4/2019 | |
| RU | 2196822 C1 | * | 1/2003 | ............. C12N 15/70 |

OTHER PUBLICATIONS

Kalamorz, et al. Journal of Bacteriology, Aug. 2011, p. 4290-4291 (Year: 2011).*
Gregoret, et al. Folding & Design vol. 3 No 2, 1997. pp. 119-126 (Year: 1997).*
Chen, Jie et. al. Improving stability of nitrile hydratase by bridging the salt—bridges in specific thermal-sensitive regions, J. of Biotech. 164(2012) 354-362.
Akimasa Miyanaga, et. al. Mutational and structural analysis of cobalt-containingnitrile hydratase on substrate and metal binding, Eur. J. Biochem. 271, 429-438 (2004).
Shi, yue e. al. High level expression of a mutated nitrile dydratase gene of *Nocardia* Sp. in recombinant *Escherichia coli*, J Tsinghua Univ (Sci Tech) 2007, vol. 47 No. 12, 2176-2179 2007.

* cited by examiner

*Primary Examiner* — Louise W Humphrey
*Assistant Examiner* — Jessica Faye Edwards
(74) *Attorney, Agent, or Firm* — IPRO, PLLC (57) ABSTRACT

The disclosure discloses a mutant of nitrile hydratase derived from *Caldalkalibacillus thermarum*, and belongs to the technical field of enzyme engineering. The nitrile hydratase mutant *Cal. t* Nhase-A20V provided by the disclosure has a half-life of about 10 min at 70° C., which does not change much compared with the thermal stability of the wild enzyme. The specific enzyme activity of the mutant *Cal. t* Nhase-A20V is 128% of that of the wild enzyme. At the same time, the mutant also has better tolerance to a substrate and a product, and the final yield of nicotinamide produced by whole-cell catalysis reaches 598 g/L. Therefore, the nitrile hydratase mutant *Cal. t* Nhase-A20V provided by the disclosure has good enzymatic properties and is beneficial to future industrial production.

10 Claims, 3 Drawing Sheets

Specification includes a Sequence Listing.

MUTANT OF NITRILE HYDRATASE DERIVED FROM *CALDALKALIBACILLUS THERMARUM*

TECHNICAL FIELD

The disclosure herein relates to a mutant of nitrile hydratase derived from *Caldalkalibacillus thermarum*, and belongs to the technical field of enzyme engineering.

BACKGROUND

Nitrile hydratase (NHase) can be used to catalyze 3-cyanopyridine into nicotinamide with higher medicinal value. Niacinamide is a vitamin and has been widely used in industries such as feed, food, and pharmacy. Nicotinamide is in great demand in the market, but the current production level of niacinamide in China is not high and the scale is small. Therefore, the use of NHase in the production of nicotinamide has great potential. However, the reaction is an exothermic process, so high temperature in the production process will affect the performance of enzyme activity. The main reason is that the high temperature affects the structure of the enzyme, leading to a decrease in enzyme activity, which in turn leads to a large amount of energy consumption and increases production costs. At the same time, both the substrate and product of the nitrile hydratase are organic matter. High-concentration organic matter will have a great destructive effect on the structure of the enzyme, causing the enzyme activity to decrease rapidly and the catalytic activity to decrease. Therefore, it is particularly important to improve the tolerance of the nitrile hydratase to substrates and products in a catalysis process of production.

At present, *Rhodococcus rhodochrous* J1 is mainly used in industrial production for catalysis to produce nicotinamide by adopting a method of substrate feeding in batches. However, the growth cycle of Rhodococcus is long, requiring 100 h, and the production efficiency is not high. The highest yield of nicotinamide is 162 g/L, and the highest yield of acrylamide is 300 g/L. There are also reports of the production of nicotinamide by recombinant bacteria, but the final product concentration is low, only 240 g/L. Therefore, obtaining nitrile hydratase with high efficiency and good tolerance to organic solvents has important application value for the industrial production of nicotinamide.

SUMMARY

The disclosure aims to provide a nitrile hydratase mutant with improved tolerance to products and substrates and application thereof.

A first objective of the disclosure is to provide a nitrile hydratase mutant containing a β subunit, an α subunit and a regulatory protein, the amino acid sequences of which are as shown in SEQ ID NO. 2, SEQ ID NO. 3, and SEQ ID NO. 4, respectively.

A second objective of the disclosure is to provide a gene encoding the mutant.

A third objective of the disclosure is to provide a vector containing the gene.

A fourth objective of the disclosure is to provide a cell expressing the nitrile hydratase mutant.

In one example of the disclosure, the cell includes *E. coli*.

In one example of the disclosure, the cell uses *E. coli* BL21 as a host and a pET-series plasmid as a vector.

In one example of the disclosure, the plasmid is pET-24 (+).

A fifth objective of the disclosure is to provide a method for improving the enzyme activity of nitrile hydratase, and the method is to mutate glycyl acid at position 20 of an α subunit of the nitrile hydratase to valine, wherein the amino acid sequence of the nitrile hydratase is as shown in SEQ ID NO. 5.

A sixth objective of the disclosure is to provide a composition containing the nitrile hydratase mutant.

In one example of the disclosure, a protective agent is included, but is not limited thereto.

A seventh objective of the disclosure is to provide application of the nitrile hydratase mutant or the cell in the production of products containing nicotinamide or acrylamide.

In one example of the disclosure, the nitrile hydratase mutant, or the cell, or the composition is used as a catalyst, and a transformation reaction is carried out with 3-cyanopyridine or acrylonitrile as the substrate.

In one example of the disclosure, 3-cyanopyridine or acrylonitrile is used as a substrate, the cell is used for fermentation, and the fermentation broth is used for whole-cell transformation to produce nicotinamide or acrylamide.

In one example of the disclosure, the $OD_{600}$ of the fermentation broth is 5-10, and the concentration of the substrate is 0.2-1 mol/L.

In one example of the disclosure, the whole-cell transformation reaction conditions are: the temperature is 25-28° C., and the mass ratio of the substrate 3-cyanopyridine to wet bacterial cells is 0.5-2.

In one example of the disclosure, the whole-cell transformation reaction conditions are: the temperature is 25-28° C., and the mass ratio of the substrate acrylonitrile to wet bacterial cells is 1-1.5.

In one example of the disclosure, the nitrile hydratase mutant is prepared as follows: an LB culture medium is inoculated with the cells expressing the nitrile hydratase mutant, culturing is performed at 35-37° C. until the $OD_{600}$ is 0.6-0.8, and then an inducer IPTG is added to carry out induction at 20-30° C. for 12-18 h.

In one example of the disclosure, the method includes the following steps: inoculating an LB expression culture medium containing kanamycin with the cells, performing culturing with shaking at 37° C. and 200 r/min until the $OD_{600}$ is 0.6-0.8, then adding an inducer IPTG to 0.1 mM, and adding $Co^{2+}$ to 0.1 mg/L to carry out induction at 25° C. for 12-18 h.

In one example of the disclosure, the method further includes the following steps: collecting the bacterial cells of the cells, disrupting the bacterial cells, collecting the supernatant, performing filtering through a membrane, and performing separation with a Strep Trap HP column to obtain the nitrile hydratase mutant.

The disclosure further provides application of the cell in the field of fermentation.

Beneficial effects: The nitrile hydratase mutant *Cal. t* Nhase-A20V provided by the disclosure has a half-life of about 10 min at 70° C., which does not change much compared with the thermal stability of the wild enzyme. The specific enzyme activity of the mutant *Cal. t* Nhase-A20V is 650 U/mg, which is 128% of that of the wild enzyme. At the same time, the mutant also has better tolerance to a substrate and a product, and the final yield of nicotinamide produced by whole-cell catalysis reaches 598 g/L. Therefore, the nitrile hydratase mutant *Cal. t* Nhase-A20V provided by the disclosure has good enzymatic properties and is beneficial to future industrial production.

DETAILED DESCRIPTION

Definition of enzyme activity (U): The amount of enzyme required to transform 3-cyanopyridine to 1 μmol/L nicotinamide per minute is defined as 1 U.

Specific enzyme activity (U/mg): The enzyme activity per milligram of NHase.

Definition of relative enzyme activity: The enzyme activity of a mutant enzyme measured at a pH of 7.4 and a temperature of 30° C. for 10 min is defined as 100%.

LB culture medium: Peptone 10 g/L, yeast extract 5 g/L, and NaCl 10 g/L.

Reaction system of nitrile hydratase: The substrate is 490 μL of 200 mM 3-cyanopyridine. 10 μL of a pure enzyme solution with a concentration of 0.5 mg/mL or 10 μL of a broth with an $OD_{600}$ of 8 is added, and the reaction is carried out at 30° C. for 10 min. Then the reaction is stopped with 500 μL of acetonitrile, and the reaction solution is centrifuged to remove precipitate. The supernatant is taken, filtered through a 0.22 μm membrane, and used as a sample for liquid phase determination.

Detection of nitrile hydratase: HPLC is used for detection; a mobile phase contains water and acetonitrile in a ratio of 1:2; the detection wavelength is 210 nm; the flow rate is 0.6 mL/min; and the chromatographic column is C18 column.

Determination of temperature stability: The wild enzyme and mutant are treated in a KPB buffer with a pH of 7.4 at 70° C. for 10 min and 30 min respectively, and the residual enzyme activity is determined. The enzyme activity of the untreated enzyme is defined as 100%, and the thermostability result is obtained.

Determination of tolerance to substrate: The wild enzyme and the mutant are diluted in a KPB buffer with a pH of 7.4 to form broths with an $OD_{600}$ of 8. After incubation at 30° C. for 30 minutes in 3-cyanopyridine with the concentrations of 0 M and 1 M respectively, the residual enzyme activity is determined and the results of tolerance to the substrate are obtained.

Determination of tolerance to product: The wild enzyme and the mutant are diluted in a KPB buffer with a pH of 7.4 to form broths with an $OD_{600}$ of 8. After incubation at 30° C. for 30 minutes in nicotinamide with the concentrations of 0 M, 1 M and 2 M respectively, the residual enzyme activity is determined and the results of tolerance to the product are obtained.

Example 1

Kinetic simulations of the nitrile hydratase (Pt NHase) derived from Pseudonocardia thermophila and the Cal. t NHase derived from Caldalkalibacillus thermarum found that some amino acids had higher RMSF values, and it was speculated that these amino acids might affect the thermal stability. Therefore, the following mutants were constructed: Cal. t NHase-A20V, Cal. t NHase-H150S (the histidine at position 150 of the β subunit with an amino acid sequence as shown in SEQ ID NO. 2 was mutated to serine), Cal. t NHase-T104A (the threonine at position 104 of the β subunit with an amino acid sequence as shown in SEQ ID NO. 2 was mutated to alanine), Cal. t NHase-S152K (the serine at position 152 of the β subunit with an amino acid sequence as shown in SEQ ID NO. 2 was mutated to lysine), and Cal. t NHase-K185A (the lysine at position 185 of the β subunit with an amino acid sequence as shown in SEQ ID NO. 2 was mutated to alanine).

(1) Construction of Mutants:

A Cal. t-NHase gene (as shown in SEQ ID NO. 1) was synthesized, and the gene was cloned at the Nde I and EcoR I restriction sites of a pET24a plasmid by Suzhou Genewiz, to obtain a pET24a-Cal. t NHase recombinant plasmid. Using pET24a-Cal. t NHase as a template, PCR was carried out with the primers shown in Table 1 under the conditions shown in Table 2. The PCR products were transformed into E. coli JM109 and sequenced by Suzhou Genewiz. The recombinant plasmids pET24a-NHase-A20V, pET24a-Cal. t Nhase-H150S, pET24a-Cal. t Nhase-T104A, pET24a-Cal. t Nhase-S152K, and pET24a-Cal. t Nhase-K185A carrying the gene encoding the mutant were obtained from the plasmids with correct sequencing results. The recombinant plasmids were transformed into E. coli BL21 strains for expression to obtain recombinant strains.

TABLE 1

Primers

| Primer | Sequence | Sequence No. |
|---|---|---|
| H150S-U | AAGAACATCAGCCCGAGTGGTCATACCC | SEQ ID NO. 6 |
| H150S-D | GACCACTCGGGCTGATGTTCTTGGTTTTCAC | SEQ ID NO. 7 |
| T104A-U | CCAGCCGGATGCCCCGACCCCGCGCCGCGAAAAC | SEQ ID NO. 8 |
| T104A-D | GGCGCGGGGTCGGGGCATCCGGCTGGGCCAG | SEQ ID NO. 9 |
| S152K-U | TCCACCCGAAGGGTCATACCCGTCTG | SEQ ID NO. 10 |
| S152K-D | GGGTATGACCCTTCGGGTGGATGTTCTTG | SEQ ID NO. 11 |
| K185A-U | GCCCATGGCGCCGGCGAAAGCCCGCAG | SEQ ID NO. 12 |
| K185A-D | GCTTTCGCCGGCGCCATGGGCATTGGCAT | SEQ ID NO. 13 |
| A20V-U | TTTTGGAGCGTGCGTGCAAAGGCTTTAG | SEQ ID NO. 14 |
| A20V-D | CCTTTGCACGCACGCTCCAAAAAGACTCC | SEQ ID NO. 15 |

TABLE 2

Whole-plasmid PCR amplification reaction system

| Regent | Amount |
|---|---|
| $ddH_2O$ | 32 μL |
| 5 × PS Buffer ($Mg^{2+}$ plus) | 10 μL |

TABLE 2-continued

Whole-plasmid PCR amplification reaction system

| Regent | Amount |
| --- | --- |
| dNTP Mixture (2 mmol/L) | 4 μL |
| P1 (10 mmol/L) | 1 μL |
| P2 (10 mmol/L) | 1 μL |
| pET24a-Cal.t NHase | 1 μL |
| Primer STAR HS DNA polymerase | 1 μL |
| Total | 50 μL |

PCR Amplification Reaction Conditions:

| | | |
| --- | --- | --- |
| 95° C. Initial denaturation | 5 min | |
| 95° C. Denaturation | 1 min | |
| 58° C. Annealing | 30 s | } 30 cycles |
| 72° C. Extension | 2 min | |
| 72° C. Extension | 10 min | |

The PCR products were identified by agarose gel electrophoresis. Then the PCR products were purified, digested and transformed into *E. coli* BL21 competent cells.

(2) 5 mL of LB culture medium (peptone 10 g/L, yeast extract 5 g/L, NaCl 10 g/L) containing kanamycin with a concentration of 50 μg/mL was inoculated with the recombinant *E. coli* strains BL21/pET24a-*Cal. t* NHase-A20V, BL21/pET24a-*Cal. t* Nhase-H150S, BL21/pET24a-*Cal. t* Nhase-T104A, BL21/pET24a-*Cal. t* Nhase-S152K, and BL21/pET24a-*Cal. t* Nhase-K185A obtained in step (1), and culturing was performed with shaking overnight at 37° C. and 200 r/min.

100 mL of LB expression culture medium (peptone 10 g/L, yeast extract 5 g/L, NaCl 10 g/L) containing kanamycin with a concentration of 50 μg/mL was inoculated with the overnight culture at an inoculum concentration of 1% (v/v), and culturing was performed at 37° C. and 200 r/min with shaking until the $OD_{600}$ was 0.6-0.8. Then an inducer IPTG was added to 0.1 mM, and $Co^{2+}$ was added to 0.1 mg/L to carry out induction at 25° C. for 12-18 h to obtain bacterial cells. The bacterial cells were centrifuged at 12,000 rpm and then collected.

(3) The recombinant bacterial cells were concentrated with a binding buffer solution (20 mmol/L $Na_2HPO_4$, 280 mmol/L NaCl, 6 mmol/L KCl) 5 times, ultrasonically disrupted, and centrifuged at 12,000 rpm for 40 min. The supernatant was filtered with a 0.22 μm filter membrane. A 1 mL strep Trap HP column was equilibrated with the binding buffer solution 10 times the column volume. Non-specifically adsorbed proteins were washed out with the binding buffer solution 15 times the column volume. The protein was eluted with 20 mM $Na_2HPO_4$, 280 mM NaCl, 6 mM KCl, and 2.5 mM dethiobiotin buffer 8 times the column volume. The samples were collected and analyzed and identified by SDS-PAGE.

Example 2

10 μL of the 0.5 mg/mL mutant enzyme purified in Example 1 was added to a 500 pi buffer reaction system, and the reaction system was treated in a metal bath at 70° C. for 0 min, 10 min, 20 min, and 30 min respectively. The residual enzyme activity was determined, wherein the enzyme activity after treatment for 0 min is defined as 100%.

Figure 1:
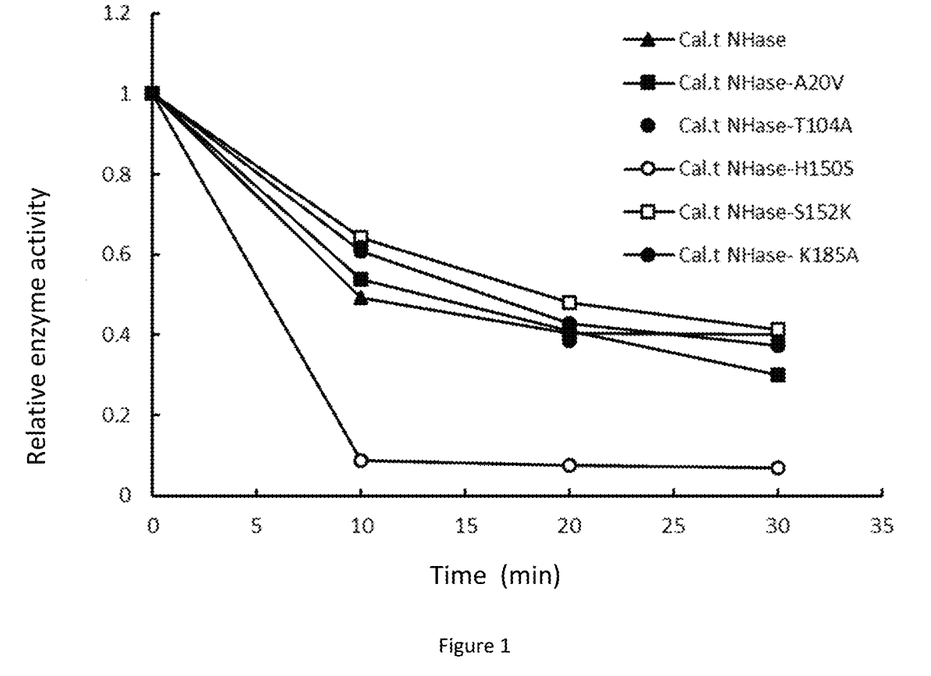
FIG. 1 shows the thermal stability of the wild enzyme and the mutant enzyme Cal. t Nhase-A20V treated at 70° C. for 10 min.

As shown in FIG. 1, it was found that when the mutant was treated at 70° C. for 10 min, the enzyme activity of the mutant enzyme *Cal. t* NHase-H150S decreased sharply, while the other mutant enzymes did not change much compared with the wild type. Therefore, the properties of the *Cal. t* NHase-H150S mutant enzyme were not studied in the follow-up study.

Example 3

Solutions of the product nicotinamide with different concentrations of 0 M and 2 M were prepared. Broths of the wild enzyme and the mutant with an $OD_{600}$ of 8 were treated in the substrate solutions with different concentrations at 30° C. for 30 min, and then the cells were resuspended in KPB and washed twice. 10 μL of samples were taken to determine the residual enzyme activity. The enzyme activity treated with the nicotinamide solution of 0 M was defined as 100%.

Figure 2:
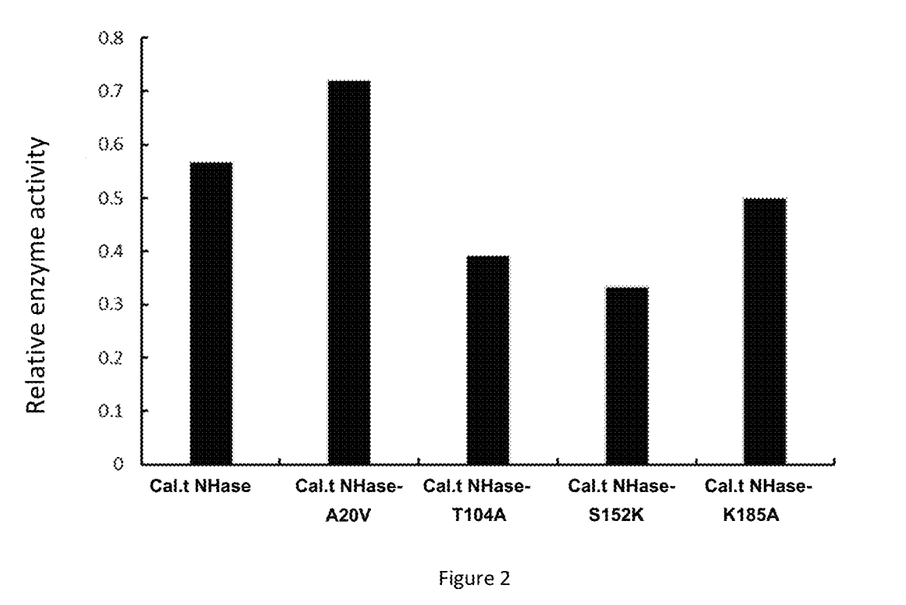
FIG. 2 shows the r of the relative enzyme activity of wild enzyme and the mutant enzyme treated at 30° C. for 30 min.

As shown in FIG. 2, the enzyme activity without treatment with a product was defined as 100%. It was found that after the mutant was treated with the product nicotinamide of 2 M for 20 min, the residual enzyme activity of the mutant enzyme *Cal. t* Nhase-A20V increased from 40% of the wild enzyme to 69%, while the residual enzyme activity of the rest mutant enzymes *Cal. t* NHase-H150S, *Cal. t* NHase-T104A, *Cal. t* NHase-S152K, and *Cal. t* NHase-K185A, compared with the wild enzyme, showed varying degrees of decline. The tolerance of the mutant enzyme *Cal. t* Nhase-A20V to a product was significantly improved, so the *Cal. t* Nhase-A20V mutant enzyme was selected for follow-up study.

Example 4

Solutions of substrate with different concentrations of 0 M and 1 M were prepared: The broths of the wild enzyme and mutants with an $OD_{600}$ of 8 were treated in solutions of substrate with different concentrations at 30° C. for 30 min. Then the cells were resuspended in KPB and washed twice. 10 μL of samples were taken to determine the residual enzyme activity. The enzyme activity treated with the solution of 0 M is defined as 100%.

Figure 3:
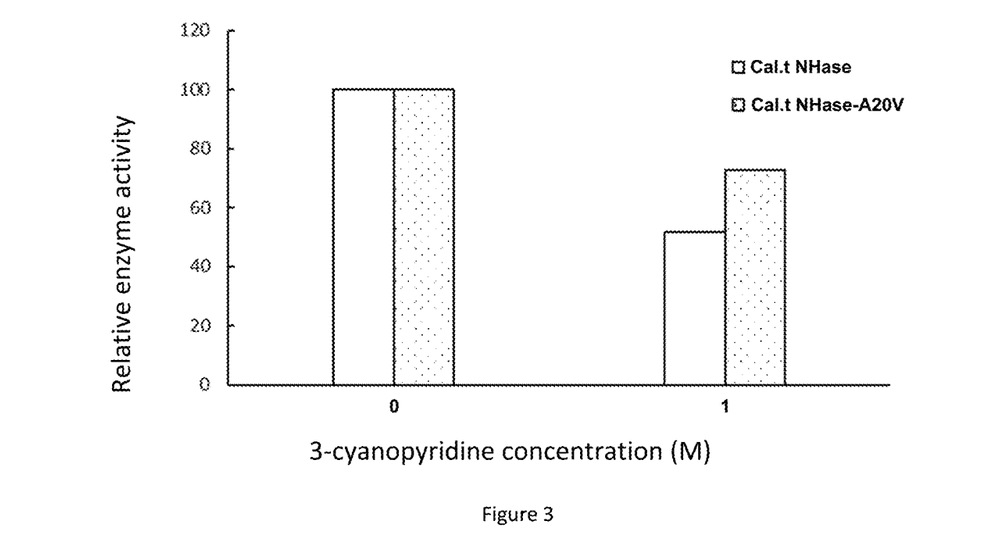
FIG. 3 shows the tolerance of the wild enzyme and the mutant enzyme Ca11 Nhase-A20V to the substrate under different concentrations of substrate 3-cyanopyridine.
Figure 4:
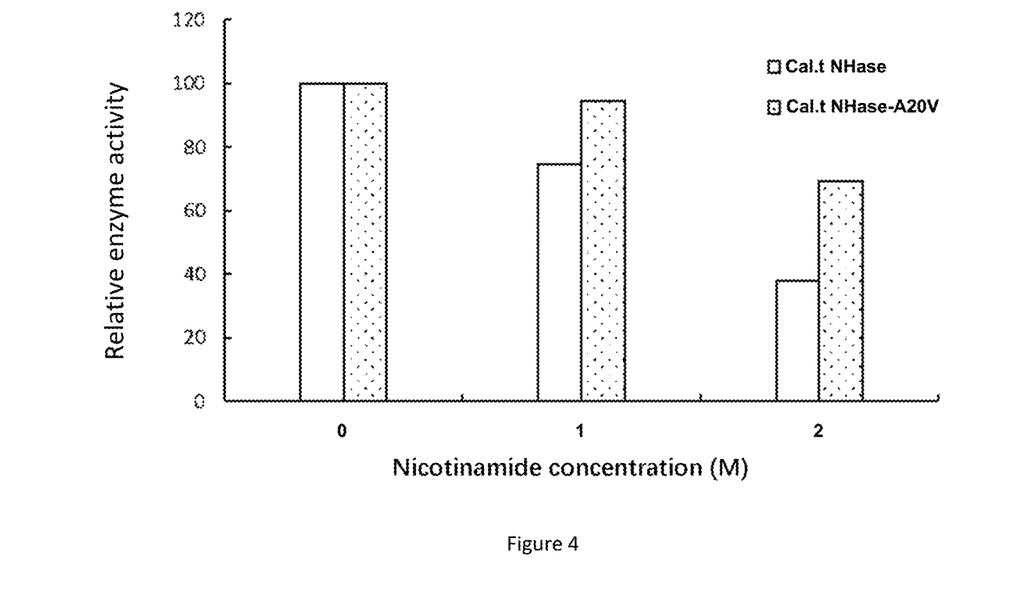
FIG. 4 shows the tolerance of the wild enzyme and the mutant enzyme Ca11 Nhase-A20V to the substrate under different concentrations of substrate nicotinamide.

As shown in FIG. 3 and FIG. 4, the enzyme activity after treatment with the substrate of 0 M was defined as 100%, and it was found that after the mutant was treated with the substrate 3-cyanopyridine of 1 M at 30° C. for 30 min, the residual enzyme activity of the mutant was increased from 52% of the wild enzyme to 72%, and the tolerance of the mutant to a substrate was significantly improved.

Example 5

Figure 5:
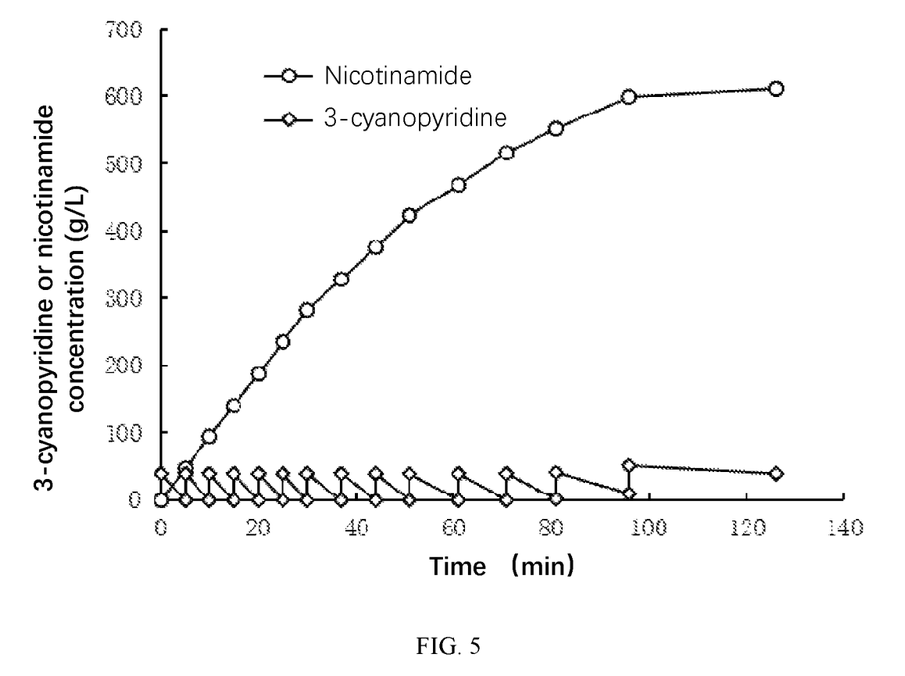
FIG. 5 shows the concentration of 3-cyanopyridine and nicotinamide in the process of enzymatic reaction from 3-cyanopyridine to nicotinamide.

The BL21/pET24a-*Cal. t* NHase-A20V broth obtained in step (2) of Example 1 was centrifuged and collected, washed with water, and centrifuged and collected again. The temperature was adjusted to 25-28° C. 3-cyanopyridine was added to the broth with an $OD_{600}$ of 8 at a final concentration of 0.4 mol/L, and stirred continuously. When the present batch of substrate reacted completely, the next batch of substrate was added. The content of each component in the reaction solution was detected by HPLC, and the concentration of nicotinamide was calculated as 598 g/L, as shown in FIG. 5.

While various aspects and embodiments have been disclosed herein, other aspects and embodiments will be apparent to those skilled in the art. The various aspects and embodiments disclosed herein are for purposes of illustra-

What is claimed is:

1. A mutant nitrile hydratase, comprising:
a β subunit,
an α subunit, and
a regulatory protein,
wherein the amino acid sequences of the β subunit, the α subunit, and the regulatory protein are SEQ ID NO: 2, SEQ ID NO: 3, and SEQ ID NO: 4, respectively, wherein the nucleotide sequence of the mutant nitrile hydratase is SEQ ID NO:1, wherein the mutant nitrile hydratase has a specific activity of 650 U/mg, and wherein the mutant nitrile hydratase is capable of catalyzing formation of nicotinamide by whole-cell catalysis up to a concentration of 598 g/L.

2. A recombinant *Escherichia coli* (E. coli), wherein the recombinant *E. coli* expresses the mutant nitrile hydratase according to claim 1.

3. The recombinant *E. coli* according to claim 2, wherein the *E. coli* is *E. coli* BL21, and wherein the recombinant *E. coli* comprises a pET-series plasmid encoding the mutant nitrile hydratase.

4. The recombinant *E. coli* according to claim 3, wherein the plasmid is pET--24(+).

5. A method for producing nicotinamide or acrylamide, comprising, incubating the mutant nitrile hydratase of claim 1 with 3-cyanopyridine or acrylonitrile as a substrate to thereby produce nicotinamide or acrylamide.

6. A method for producing nicotinamide or acrylamide comprising: providing the recombinant *E. coli* of claim 2, fermenting the recombinant *E. coli* in a fermentation broth, and adding 3-cyanopyridine or acrylonitrile as a substrate to the fermentation broth, thereby producing nicotinamide or acrylamide.

7. The method according to claim 6, wherein $OD_{600}$ of the fermentation broth after fermentation is 5 to 10, and the concentration of the substrate is 0.2 mol/L to 1 mol/L.

8. The method according to claim 6, wherein the fermentation is performed at 25° C. to 28° C., and wherein the mass ratio of the substrate 3-cyanopyridine to wet bacterial cells is 0.5 to 2.

9. The method according to claim 6, wherein the fermentation is performed at 25° C. to 28° C., and wherein the mass ratio of the substrate acrylonitrile to wet bacterial cells is 1 to 1.5.

10. The method according to claim 6, wherein the mutant nitrile hydratase is prepared as follows:
    inoculating the recombinant *E. coli* in Luria Broth (LB) culture medium, culturing at 35° C. to 37° C. until the $OD_{600}$ is 0.6 to 0.8, and adding isopropyl-β-D-1-thio-galactopyranoside (IPTG) for induction at 20° C. to 30° C. for 12 hours to 18 hours.

\* \* \* \* \*

SEQUENCE LISTING

<160> NUMBER OF SEQ ID NOS: 15

<210> SEQ ID NO 1
<211> LENGTH: 1708
<212> TYPE: DNA
<213> ORGANISM: Caldalkalibacillus thermarum

<400> SEQUENCE: 1

```
atgaatggca ttcatgattt aggtggcatg gatggctttg caagatcat ccgcgaagag      60
aacgaaccgc tgttccacaa agactgggag cgcattgcct ttggtttatt aattggtacc    120
gccggtcaag gtctgtacaa tttagatgag ttccgccatg ccattgaacg catgaacccg    180
gtggactatt taaccagcgg ttattatggc cactgggtgg ccagcattgc aactttactg    240
gtggaaaaag cattttaga tgccagtgaa ctggtgagcc gcacccagac ctatctggcc    300
cagccggata caaaaacccc gcgccgcgaa acccggaac tggtgaacca tctggagcaa    360
gttattaagg tgggtgttag caccgtgcgc gaagttagta gcgccccgcg ctttaacgtg    420
ggtgaccgcg tgaaaaccaa gaacatccac ccgagtggtc atacccgtct gccgcgctat    480
gcccgcgata gtatggcgt gatcgcaatg taccacggtg cccatgtgtt tccggatgcc    540
aatgcccatg gcaaaggcga aagcccgcag catttatact gcattcgctt cgaagccaac    600
gaactgtggg gcattcaaca aggtgaagcc gtgtacatcg atctgtggga gagctatctg    660
gaaccggtta gccattaaaa ggagatatag atatgaaaga taacaacaaa gtgcatcacc    720
accacccgca tccggagtct ttttggagcg cccgtgcaaa ggctttagag tctttactga    780
ttgagaaagg cattctgagc agcgatgcca ttgatcgcgt tgtgcagcac tatgagcatg    840
aactgggtcc gatgaacggt gccaaagttg tggccaaggc ttggaccgat ccggccttta    900
aacagcgttt actggaagat ccggagaccg ttctgcgtga actgggttat tatggtttac    960
aaggtgaaca tatccgcgtg gtgggagaaca ccgataccgt gcacaacgtg gtggtgtgca   1020
ccttatgtag ctgctatccg tggccgctgc tgggttacc gcccgcttgg tataaagaac   1080
cgacctatcg cagccgcatt gttaaagagc gcgtaaagt gctgcgcgaa gaatttggtt   1140
tagatttacc ggatacagtt gagattcgcg tgtgggatag cagcagtgaa atgcgctaca   1200
tggtgctgcc gcaacgcccg gaaggtaccg aaggcatgac cgaagaagaa ctggcaaaaa   1260
tcgtgacccg cgacagcatg attggcgtgg caaaagtgca gccgagcagc gtgaccgttc   1320
gctaaaagga gatatagata tggagaaaaa ttgcgtgagc cagagcgtgg atagcaaaat   1380
cgcctatctg ccggaaagcg cagcaccgcc gcgcaaaaac ggcgaactgg tgttcgaaga   1440
accgtgggaa cgccgcagct ttggtatggc tttagcttta tatgaggaaa agcgctatac   1500
cagctgggat gactttcgca cccgtttaat tcaagaaatc gccaaatggg agagcagcga   1560
gaaccaagat aaactggatt ggaactatta tgaacattgg ctggccgctt tagaacagct   1620
ggtggtggaa accggcatga tcgataaaca cgacattgac gcccgcacca aggagttttt   1680
aagcggcgaa cgcgatgagt tttttaa                                       1708
```

<210> SEQ ID NO 2
<211> LENGTH: 225
<212> TYPE: PRT
<213> ORGANISM: Caldalkalibacillus thermarum

<400> SEQUENCE: 2

```
Met Asn Gly Ile His Asp Leu Gly Gly Met Asp Gly Phe Gly Lys Ile
1               5                   10                  15

Ile Arg Glu Glu Asn Glu Pro Leu Phe His Lys Asp Trp Glu Arg Ile
            20                  25                  30

Ala Phe Gly Leu Leu Ile Gly Thr Ala Gly Gln Gly Leu Tyr Asn Leu
        35                  40                  45

Asp Glu Phe Arg His Ala Ile Glu Arg Met Asn Pro Val Asp Tyr Leu
    50                  55                  60

Thr Ser Gly Tyr Tyr Gly His Trp Val Ala Ser Ile Ala Thr Leu Leu
65                  70                  75                  80

Val Glu Lys Gly Ile Leu Asp Ala Ser Glu Leu Val Ser Arg Thr Gln
                85                  90                  95

Thr Tyr Leu Ala Gln Pro Asp Thr Lys Thr Pro Arg Arg Glu Asn Pro
            100                 105                 110

Glu Leu Val Asn His Leu Glu Gln Val Ile Lys Val Gly Val Ser Thr
        115                 120                 125

Val Arg Glu Val Ser Ser Ala Pro Arg Phe Asn Val Gly Asp Arg Val
130                 135                 140

Lys Thr Lys Asn Ile His Pro Ser Gly His Thr Arg Leu Pro Arg Tyr
145                 150                 155                 160

Ala Arg Asp Lys Tyr Gly Val Ile Ala Met Tyr His Gly Ala His Val
                165                 170                 175

Phe Pro Asp Ala Asn Ala His Gly Lys Gly Glu Ser Pro Gln His Leu
            180                 185                 190

Tyr Cys Ile Arg Phe Glu Ala Asn Glu Leu Trp Gly Ile Gln Gln Gly
        195                 200                 205

Glu Ala Val Tyr Ile Asp Leu Trp Glu Ser Tyr Leu Glu Pro Val Ser
    210                 215                 220

His
225
```

<210> SEQ ID NO 3
<211> LENGTH: 210
<212> TYPE: PRT
<213> ORGANISM: Caldalkalibacillus thermarum

<400> SEQUENCE: 3

```
Met Lys Asp Asn Asn Lys Val His His His Pro His Pro Glu Ser
1               5                   10                  15

Phe Trp Ser Val Arg Ala Lys Ala Leu Glu Ser Leu Leu Ile Glu Lys
            20                  25                  30

Gly Ile Leu Ser Ser Asp Ala Ile Asp Arg Val Val Gln His Tyr Glu
        35                  40                  45

His Glu Leu Gly Pro Met Asn Gly Ala Lys Val Ala Lys Ala Trp
    50                  55                  60

Thr Asp Pro Ala Phe Lys Gln Arg Leu Leu Glu Asp Pro Glu Thr Val
65                  70                  75                  80

Leu Arg Glu Leu Gly Tyr Tyr Gly Leu Gln Gly Glu His Ile Arg Val
                85                  90                  95

Val Glu Asn Thr Asp Thr Val His Asn Val Val Val Cys Thr Leu Cys
            100                 105                 110

Ser Cys Tyr Pro Trp Pro Leu Leu Gly Leu Pro Pro Ala Trp Tyr Lys
        115                 120                 125
```

Glu Pro Thr Tyr Arg Ser Arg Ile Val Lys Glu Pro Arg Lys Val Leu
            130                 135                 140

Arg Glu Glu Phe Gly Leu Asp Leu Pro Asp Thr Val Glu Ile Arg Val
145                 150                 155                 160

Trp Asp Ser Ser Glu Met Arg Tyr Met Val Leu Pro Gln Arg Pro
            165                 170                 175

Glu Gly Thr Glu Gly Met Thr Glu Glu Leu Ala Lys Ile Val Thr
            180                 185                 190

Arg Asp Ser Met Ile Gly Val Ala Lys Val Gln Pro Ser Ser Val Thr
            195                 200                 205

Val Arg
    210

<210> SEQ ID NO 4
<211> LENGTH: 122
<212> TYPE: PRT
<213> ORGANISM: Caldalkalibacillus thermarum

<400> SEQUENCE: 4

Met Glu Lys Asn Cys Val Ser Gln Ser Val Asp Ser Lys Ile Ala Tyr
1               5                   10                  15

Leu Pro Glu Ser Ala Ala Pro Pro Arg Lys Asn Gly Glu Leu Val Phe
            20                  25                  30

Glu Glu Pro Trp Glu Arg Arg Ser Phe Gly Met Ala Leu Ala Leu Tyr
        35                  40                  45

Glu Glu Lys Arg Tyr Thr Ser Trp Asp Phe Arg Thr Arg Leu Ile
50                  55                  60

Gln Glu Ile Ala Lys Trp Glu Ser Ser Glu Asn Gln Asp Lys Leu Asp
65                  70                  75                  80

Trp Asn Tyr Tyr Glu His Trp Leu Ala Ala Leu Glu Gln Leu Val Val
                85                  90                  95

Glu Thr Gly Met Ile Asp Lys His Asp Ile Asp Ala Arg Thr Lys Glu
            100                 105                 110

Phe Leu Ser Gly Glu Arg Asp Glu Phe Phe
        115                 120

<210> SEQ ID NO 5
<211> LENGTH: 210
<212> TYPE: PRT
<213> ORGANISM: Caldalkalibacillus thermarum

<400> SEQUENCE: 5

Met Lys Asp Asn Asn Lys Val His His His Pro His Pro Glu Ser
1               5                   10                  15

Phe Trp Ser Ala Arg Ala Lys Ala Leu Glu Ser Leu Leu Ile Glu Lys
            20                  25                  30

Gly Ile Leu Ser Ser Asp Ala Ile Asp Arg Val Gln His Tyr Glu
        35                  40                  45

His Glu Leu Gly Pro Met Asn Gly Ala Lys Val Val Ala Lys Ala Trp
50                  55                  60

Thr Asp Pro Ala Phe Lys Gln Arg Leu Leu Glu Asp Pro Glu Thr Val
65                  70                  75                  80

Leu Arg Glu Leu Gly Tyr Tyr Gly Leu Gln Gly Glu His Ile Arg Val
                85                  90                  95

Val Glu Asn Thr Asp Thr Val His Asn Val Val Val Cys Thr Leu Cys
            100                 105                 110

Ser Cys Tyr Pro Trp Pro Leu Leu Gly Leu Pro Pro Ala Trp Tyr Lys
            115                 120                 125

Glu Pro Thr Tyr Arg Ser Arg Ile Val Lys Glu Pro Arg Lys Val Leu
130                 135                 140

Arg Glu Glu Phe Gly Leu Asp Leu Pro Asp Thr Val Glu Ile Arg Val
145                 150                 155                 160

Trp Asp Ser Ser Glu Met Arg Tyr Met Val Leu Pro Gln Arg Pro
                165                 170                 175

Glu Gly Thr Glu Gly Met Thr Glu Glu Leu Ala Lys Ile Val Thr
            180                 185                 190

Arg Asp Ser Met Ile Gly Val Ala Lys Val Gln Pro Ser Ser Val Thr
            195                 200                 205

Val Arg
    210

<210> SEQ ID NO 6
<211> LENGTH: 28
<212> TYPE: DNA
<213> ORGANISM: Artificial sequence
<220> FEATURE:
<223> OTHER INFORMATION: synthetic DNA

<400> SEQUENCE: 6
aagaacatca gcccgagtgg tcataccc                                      28

<210> SEQ ID NO 7
<211> LENGTH: 31
<212> TYPE: DNA
<213> ORGANISM: Artificial sequence
<220> FEATURE:
<223> OTHER INFORMATION: synthetic DNA

<400> SEQUENCE: 7
gaccactcgg gctgatgttc ttggttttca c                                  31

<210> SEQ ID NO 8
<211> LENGTH: 34
<212> TYPE: DNA
<213> ORGANISM: Artificial sequence
<220> FEATURE:
<223> OTHER INFORMATION: synthetic DNA

<400> SEQUENCE: 8
ccagccggat gccccgaccc cgcgccgcga aaac                               34

<210> SEQ ID NO 9
<211> LENGTH: 31
<212> TYPE: DNA
<213> ORGANISM: Artificial sequence
<220> FEATURE:
<223> OTHER INFORMATION: synthetic DNA

<400> SEQUENCE: 9 ggcgcgggt cggggcatcc ggctgggcca g                                   31

<210> SEQ ID NO 10
<211> LENGTH: 31
<212> TYPE: DNA
<213> ORGANISM: Artificial sequence
<220> FEATURE:
<223> OTHER INFORMATION: synthetic DNA

```
<400> SEQUENCE: 10
ggcgcggggt cggggcatcc ggctgggcca g                                    31

<210> SEQ ID NO 11
<211> LENGTH: 29
<212> TYPE: DNA
<213> ORGANISM: Artificial sequence
<220> FEATURE:
<223> OTHER INFORMATION: synthetic DNA

<400> SEQUENCE: 11
gggtatgacc cttcgggtgg atgttcttg                                       29

<210> SEQ ID NO 12
<211> LENGTH: 27
<212> TYPE: DNA
<213> ORGANISM: Artificial sequence
<220> FEATURE:
<223> OTHER INFORMATION: synthetic DNA

<400> SEQUENCE: 12
gcccatggcg ccggcgaaag cccgcag                                         27

<210> SEQ ID NO 13
<211> LENGTH: 29
<212> TYPE: DNA
<213> ORGANISM: Artificial sequence
<220> FEATURE:
<223> OTHER INFORMATION: synthetic DNA

<400> SEQUENCE: 13
gctttcgccg gcgccatggg cattggcat                                       29

<210> SEQ ID NO 14
<211> LENGTH: 28
<212> TYPE: DNA
<213> ORGANISM: Artificial sequence
<220> FEATURE:
<223> OTHER INFORMATION: synthetic DNA

<400> SEQUENCE: 14
ttttggagcg tgcgtgcaaa ggctttag                                        28

<210> SEQ ID NO 15
<211> LENGTH: 29
<212> TYPE: DNA
<213> ORGANISM: Artificial sequence
<220> FEATURE:
<223> OTHER INFORMATION: synthetic DNA

<400> SEQUENCE: 15
cctttgcacg cacgctccaa aaagactcc                                       29
```